Dec. 9, 1952 K. E. WILLIAMS Plant Pat. 1,154
IVY PLANT
Filed Sept. 28, 1951
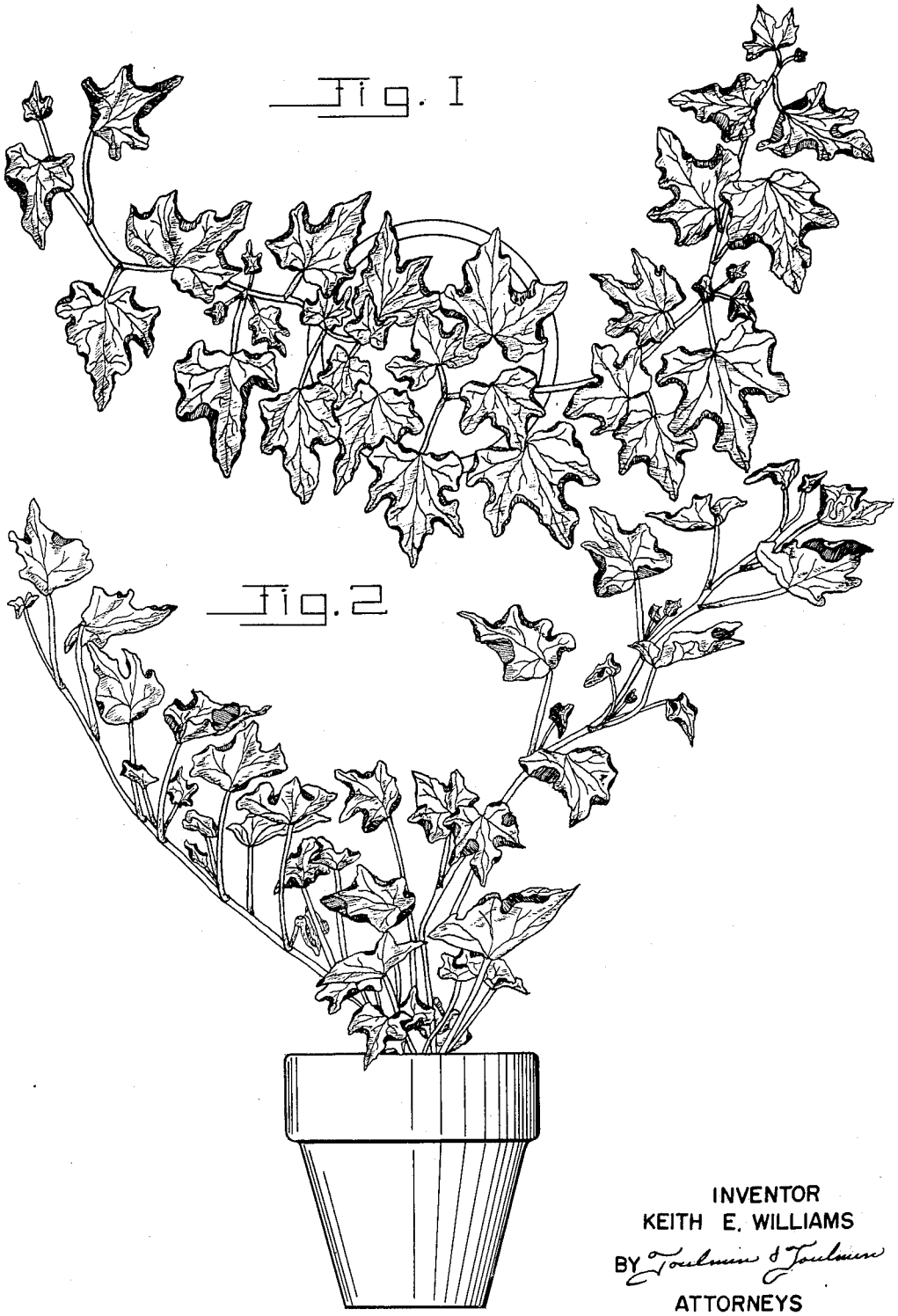
INVENTOR
KEITH E. WILLIAMS
BY Toulmin & Toulmin
ATTORNEYS Patented Dec. 9, 1952

Plant Pat. 1,154

UNITED STATES PATENT OFFICE 1,154

IVY PLANT

Keith E. Williams, Springfield, Ohio

Application September 28, 1951, Serial No. 248,804

1 Claim. (Cl. 47—59)

My present discovery relates to a new and distinct variety of ivy plant which originated as a sport from Barcafer's Ideal (not patented) in my green houses at Springfield, Ohio. I have reproduced the new variety asexually from cuttings in the same gardens in approximately 500 specimens and its characteristics have proved to be permanent.

The accompanying illustrations rendered in black and white represent my discovery as follows:

Figure 1 is a plan view of the ivy plant; and

Figure 2 is a side elevation of the ivy of Figure 1.

The new variety attains in the main stem an upright growth in the early stages of up to about 10 inches, becoming pendulous as the length increases, and having distinct self branching characteristics producing at nearly every node of the stem new shoots consisting of several small light-colored fine leaves. The length between nodes is generally about 1 inch and the main stem has attained an overall length of about 12 feet and may be considered to grow to an indefinite length. The growth is rapid and vigorous similar to that of other ivies, and thrives as a house plant.

The lengths of the petioles vary from about one to nearly two inches and are slender, having a slightly purplish tint at the portion adjacent the main stem and being light green (Maerz and Paul Plate No. 20 L–3) in the upper reaches.

One of the most outstanding features of the leaves is the lacy appearance created by the novel edges which are upwardly turned from the surface of the leaf particularly at the portions of the edges defining the lateral sides of each of the lobes, the upwardly turned portions of adjacent lobes merging together to form a continuous predominant upturned portion connecting adjacent lobes. Thus, as the leaves are usually five lobed as shown in the accompanying figures, distinct upturned portions appear between the terminal lobe and the lateral lobes, the upturned edge tapering off very gradually as it approaches the lobe tips but retaining the curled effect throughout. Similar upturned portions are present between the lateral lobes and the basal lobes and the lower extremity of the basal lobe is likewise upturned. Thus the overall appearance is lacy in character occasioned by the upwardly turned, curling edges.

As noted the leaves are normally five lobed, the terminal lobe having a length of about 1 to 1¼ inches and a width at the upper side of the lateral lobes of about ½ inch or slightly less. The lateral lobes have a length of less than about ¾ inch and a width of about ¼ inch. The basal lobes have a length of about ½ inch and the width is slightly greater than that of the lateral lobes being also about ½ inch. Accordingly the leaf width measured across the basal lobes is nearly as great, and in some instances is as great as the length of the terminal lobe. The actual measurements of the leaf are given for illustrative and comparative purposes, as they will vary to some extent with soil, moisture and climatic conditions.

The leaf is deep cut between the terminal and lateral lobes and not quite as deeply cut between the lateral and basal lobes. There are five distinct veins in the leaf slightly raised from the surface which run from the base of the leaf to the apex of each lobe. Branched veins spring from these distinct veins and contribute to some degree to the contrast effect established by the light veins (Maerz and Paul Plate No. 19 F–5) and the dark green (Maerz and Paul Plate No. 23 H–9) older leaves. The surface of the leaf is otherwise glossy and the texture leathery. In general the color of the leaf is substantially the usual ivy green and is uniformly colored.

The new variety has no reproductive organs and does not reproduce fruit or flowers.

The new variety is distinct from the parent the leaves of which are larger and not upwardly extending or curled.

Having thus disclosed my invention I claim:

A new and distinct variety of ivy plant, as herein shown and described, characterized particularly by its plurality of lobes, the edges of which are curled and predominantly extend upwardly along the lateral sides defining each of the lobes to give a lacy appearance; and by its habit of freely self branching without trimming.

KEITH E. WILLIAMS.

No references cited.